United States Patent [19]

Shapland et al.

[11] Patent Number: 5,499,971
[45] Date of Patent: Mar. 19, 1996

[54] METHOD FOR IONTOPHORETICALLY DELIVERING DRUG ADJACENT TO A HEART

[75] Inventors: James E. Shapland, Shoreview, Minn.; Keith R. Hildebrandt, Houlton, Wis.; Mark B. Knudson, Shoreview, Minn.

[73] Assignee: Cortrak Medical, Inc., Minneapolis, Minn.

[21] Appl. No.: 166,737

[22] Filed: Dec. 14, 1993

Related U.S. Application Data

[63] Continuation of Ser. No. 957,209, Oct. 6, 1992, abandoned, which is a continuation-in-part of Ser. No. 937,464, Aug. 28, 1992, abandoned, which is a continuation-in-part of Ser. No. 705,731, May 24, 1991, abandoned, which is a continuation-in-part of Ser. No. 637,299, Jan. 3, 1991, abandoned, which is a continuation-in-part of Ser. No. 538,961, Jun. 15, 1990, abandoned.

[51] Int. Cl.$^6$ .................................................. A61N 1/30
[52] U.S. Cl. ............................................. 604/53; 604/21
[58] Field of Search ........................... 604/20–22, 52, 604/53, 96–103; 601/2; 607/5, 7, 72, 120

[56] References Cited

U.S. PATENT DOCUMENTS

| 3,542,014 | 11/1970 | Peronneau | 128/2 |
| 3,886,950 | 6/1975 | Ukkestad et al. | 607/5 |

(List continued on next page.)

FOREIGN PATENT DOCUMENTS

| 2582946 | 12/1986 | France . | |
| 3915636 | 4/1990 | Germany . | |
| 645273 | 9/1984 | Switzerland . | |
| 1069827 | of 0000 | U.S.S.R. | 604/20 |
| 1146057 | 3/1985 | U.S.S.R. | 604/20 |
| 9116945 | 11/1991 | WIPO . | |
| WO91/19529 | 12/1991 | WIPO . | |
| 9207605 | 5/1992 | WIPO | 604/20 |

OTHER PUBLICATIONS

T. Bagniefski et al., "A Comparison of Pulsed and Continuous Current Iontophoresis," *Journal of Controlled Release*, 11 (1990), pp. 113–122.

L. A. Geddes et al. "Response to Passage of Electric Current Through the Body," *Journal of the Association for the Advancement of Medical Instrumentation*, vol. 5, No. 1, Jan. Feb. 1971.

Copy of International Search Report for PCT/US92/10805.

Medical Instrumentation, The Mechanism Underlying Sudden Death from Electric Shock, L. A. Geddes, ME, Ph.D., FACC, J. D. Bourland, Ph.D. and G. Ford, EE, Nov.–Dec. 1986, vol. 20, No. 6, pp. 303–315.

*Primary Examiner*—C. Fred Rosenbaum
*Assistant Examiner*—Mark Bockelman
*Attorney, Agent, or Firm*—Merchant, Gould, Smith, Edell, Welter & Schmidt

[57] ABSTRACT

A drug delivery apparatus and method for iontophoretically delivering a drug locally to internal body tissue. The iontophoretic delivery apparatus and method include a current source producing a net flow of current in a desired direction with high frequency waveforms which enhance delivery and minimize side effects typically associated with iontophoresis.

The invention contemplates positioning a drug delivery device in a body passageway or within body tissue and then selectively introducing a selected drug so that it is iontophoretically transported across a drug transport wall of the device for direct contact with the passageway wall or body tissue. A further aspect of the present invention involves treating a dilated vessel in the area of a stenotic lesion with a fixative or other drug to render the vessel biologically inert and to form a biological stent or prevent restenosis using specifically selected drugs. A still further aspect of the present invention involves treating a tumor or local or regional tissue mass with antitumor sensitizing agents, biological modifiers, antibiotics or other types of drugs by iontophoretic delivery of the drug to the tumor or tissue area directly or through the passageway wall.

10 Claims, 4 Drawing Sheets

U.S. PATENT DOCUMENTS

| | | | |
|---|---|---|---|
| 4,456,012 | 6/1984 | Lattin | 128/420 |
| 4,787,888 | 11/1988 | Fox | 604/20 |
| 4,936,281 | 6/1990 | Stasz | 604/22 |
| 4,976,711 | 12/1990 | Parins et al. | 604/48 |
| 5,041,107 | 8/1991 | Heil, Jr. | 604/891.1 |
| 5,042,975 | 8/1991 | Chien et al. | 604/20 |
| 5,047,028 | 9/1991 | Qian | 128/786 |
| 5,087,243 | 2/1992 | Avitall | 604/20 |
| 5,236,413 | 8/1993 | Feiring | 604/21 |

METHOD FOR IONTOPHORETICALLY DELIVERING DRUG ADJACENT TO A HEART

REFERENCE TO CO-PENDING APPLICATIONS

This is a continuation, of application Ser. No. 07/957,209, filed Oct. 6, 1992, now abandoned, which is a continuation-in-part of the U.S. patent application Ser. No. 07/937,464 titled DRUG DELIVERY APPARATUS AND METHOD, filed on Aug. 28, 1992 by James E. Shapland, Mark B. Knudson, and Jin Shimada now abandoned, which is a continuation-in-part of application Ser. No. 07/705,731, filed May 24, 1991, now abandoned, which is a continuation-in-part of application Ser. No. 637,299, filed Jan. 3, 1991 now abandoned, which in turn is a continuation-in-part of application Ser. No. 538,961, filed Jun. 15, 1990 now abandoned; all of which are hereby incorporated by reference.

BACKGROUND OF THE INVENTION

1. Field of the Invention

The present invention relates generally to a drug delivery apparatus and method for selectively and locally delivering a drug to internal body tissue. More specifically, the present invention relates to an apparatus and method for providing a net flow of electrical current in a desired direction for iontophoresis in conjunction with a catheter to selectively and locally deliver a drug to internal body tissue.

2. Description of the Related Art

Many techniques exist for delivering drugs or other medicaments to body tissue. These include, among others, oral administration, injection directly into body tissue such as through an intramuscular injection or the like, topical or transcutaneous administration where the drug is passively absorbed, or caused to pass, into or across the skin or other surface tissue and intravenous administration which involves introducing a selected drug directly into the blood stream.

Except for topical or transcutaneous administration, the above drug delivery systems tend to be systemic. In other words, administration of the drug is delivered throughout the body by the blood stream. Although transcutaneous drug delivery systems tend to be localized delivery systems in that the drug is delivered locally to a selected area, such drug delivery systems are also, by definition, limited to application of a drug externally through the patient's skin or other surface tissue. Thus, the above described drug delivery systems are generally not appropriate for the localized treatment of internal body tissue.

Although many medical situations are satisfactorily treated by the general systemic administration of a drug, there are many treatments which could be facilitated and/or improved by the ability to deliver or administer a drug locally to a selected portion of internal body tissue, without appreciably affecting the surrounding tissue.

One example is the ability to treat the dilated vessel in percutaneous transluminal coronary angioplasty (PTCA), and thus limit or prevent restenosis. In PTCA, catheters are inserted into the cardiovascular system under local anesthesia and an expandable balloon portion is then inflated to compress the atherosclerosis and dilate the lumen of the artery. Despite the general success of such PTCA procedures, high restenosis rates (reported to be as high as 47%) continue to be a major problem. Various techniques have been tried to treat stenosed vessels including the use of lasers, application of heat and the use of intravascular stents. However, many of these are still under investigation with mixed results, while others have generally not been successful. The ability to administer a drug locally to the dilated portion of the artery in PTCA procedures, without significantly affecting other tissues, would greatly enhance the ability to address the restenosis problem.

A second example of specific application for a local drug delivery system for delivering a drug to an internal body tissue is in the treatment of cancerous tumors or the like. In the treatment of such tumors, an objective is to administer the drug so that it localizes, as much as possible, in the tumor itself. Such drugs are commonly administered systemically through the blood stream. Various means are then utilized for causing the drug to localize in the cancer tumor. Nevertheless, significant portions of the drug still circulate through the blood stream, thereby affecting noncancerous tissue, producing undesirable side effects, and limiting the dosages of the drug which can be safely administered.

Also known is the use of electrophoresis (iontophoresis) to enhance transdermal drug delivery. Known techniques of transdermal iontophoresis have used direct current to promote the delivery of ionic molecules across the skin. In addition, internal iontophoretic drug delivery methods have also disclosed the use of an unspecified source of direct current as well. See, for example, U.S. Pat. No. 5,041,107 to Heil and SU-1069827 to IevIev.

Problems are, however, associated with introducing an electrical current into the body, including muscle stimulation and contraction as well as pain or other unwanted sensations. More importantly, the problem of cardiac arrhythmia (irregular rhythm) can easily arise when electrical current passes through the heart. The current source causing that problem can originate from an external source, within the heart itself, or adjacent to the heart—such as from a coronary artery.

It is known that intensity (current density), frequency, waveform and duration of the electrical current used in iontophoresis have an effect on whether cardiac arrhythmias and other problems will occur as well as the magnitude of those reactions. The threshold at which ventricular fibrillation occurs with various transthoracic and intracardiac electrical levels is known to increase with higher frequency currents (i.e., greater than 100 Hz). The threshold of sensation also increases with higher frequencies. The above observations were made using a sinusoidal alternating current set at various frequencies.

The use of alternating current to accomplish drug delivery through iontophoresis is, however, not very effective. By its very nature, a sinusoidal alternating current has increasing and decreasing current, to the point where flow can stop or actually reverse direction, thereby hampering the drug delivery effect.

One attempt to minimize the risk of iontophoresis-induced arrhythmias is disclosed in U.S. Pat. No. 5,087,243. An implanted myocardial iontophoresis patch system is disclosed there in which a pulsed current is supplied to the anodal patch. The pulses are synchronized with ventricular depolarization to avoid the interval during which the heart is vulnerable to electrically induced arrhythmias or unnatural heart rhythms. To accomplish that, the system requires instrumentation to sense the natural heartbeat of the patient. In addition, even these precautions may not prevent arrhythmias if higher iontophoretic currents are used (e.g., greater than 1 $mA/cm^2$). Also, the disclosed preferred 80–100 msec pulses will not prevent vascular muscle stimulation resulting in vaso-constriction and may cause other unwanted stimulation or sensations.

Accordingly, there is a need in the art for a method and apparatus for delivering a drug selectively and locally to internal body tissue using iontophoresis in conjunction with a catheter, without significantly affecting other tissue or inducing cardiac arrhythmias or other unwanted effects. There is a further need for such a system and method for the localized treatment of internal body tissues to limit restenosis following PTCA, to treat cancerous tumors or the like, or to treat various other medical situations using iontophoresis in conjunction with a catheter, without inducing vascular stimulation and spasms, cardiac arrhythmias or other unwanted effects.

SUMMARY OF THE INVENTION

In accordance with the present invention, an apparatus and method are provided for delivering a drug or combination of drugs selectively and locally to internal body tissue using iontophoresis in conjunction with a catheter, without inducing cardiac arrhythmias or other unwanted effects. More specifically, the invention involves an apparatus and method for iontophoretically delivering a drug or combination of drugs substantially transversely to a body passageway such as blood vessel, urinary tract, intestinal tract, kidney ducts, etc., to treat a localized region of the passageway itself and/or tissue located adjacent to the passageway. Also contemplated is delivery of a drug or combination of drugs directly to internal body tissue using the apparatus of the present invention.

In the preferred embodiment, the apparatus includes a flexible member adapted for insertion into the body passageway or tissue and a drug delivery means connected with the flexible member for delivering the drug to or through a local area of the passageway wall or tissue. The drug delivery means includes a drug transport wall for engagement with a local area of the passageway wall or tissue and a drug chamber for receiving a selected drug. The chamber is defined in part by the drug transport wall which is constructed of a material that permits selective transport of a drug therethrough, i.e. constructed of at least perforated, permeable, microporous or semipermeable material through which the drug is intended to selectively pass, that is, selectively permeable.

The apparatus and method of the present invention includes iontophoresis means connected to the drug delivery means to provide waveforms which iontophoretically transport drugs or other medicaments across the selectively permeable membrane.

The preferred waveforms can include, among others, square waves, rectangular waves, saw-toothed waves, sinusoidal waves which do not reverse polarity, and rectified sinusoidal waves. Also contemplated are modified rectangular waveforms which reverse polarity, but offer a net current flow in a desired direction.

Regardless of the specific waveform chosen, the preferred frequency of the waves is 200 Hz–100 kHz, most preferably 5–15 kHz.

The iontophoresis means of the present invention overcomes the disadvantages associated with known internal iontophoretic delivery methods and apparatus. In particular, the high frequency waveforms of the present invention maximize iontophoretic delivery in conjunction with a catheter while minimizing the negative side effects associated with iontophoresis. Those side effects include cardiac arrhythmias, muscle stimulation or other unwanted side effects.

These and other advantages and features of the present invention will become apparent with reference to the drawings, the description of the preferred embodiment and method and the appended claims.

DESCRIPTION OF THE PREFERRED AND ALTERNATE EMBODIMENTS AND METHODS

FIGS. 1–6 illustrate the preferred and various alternate designs of the drug delivery apparatus in accordance with the present invention. In general, this apparatus provides a means and a system for delivering a drug or combination of drugs to, or through, a localized area of a passageway in order to treat the localized area of the passageway or to treat a localized area of tissue located adjacent to the passageway, with minimal, if any, undesirable effect on other body tissue. The drug delivery apparatus includes a modified catheter balloon design which can be used in conjunction with existing catheters. The term catheter as used in the present application is intended to broadly include any medical device designed for insertion into a body passageway to permit injection or withdrawal of fluids, to keep a passage open or for any other purpose. It is contemplated that the drug delivery apparatus of the present invention has applicability for use with any body passageways including, among others, blood vessels, urinary tract, intestinal tract, kidney ducts, wind pipe and the like.

Figure 5:
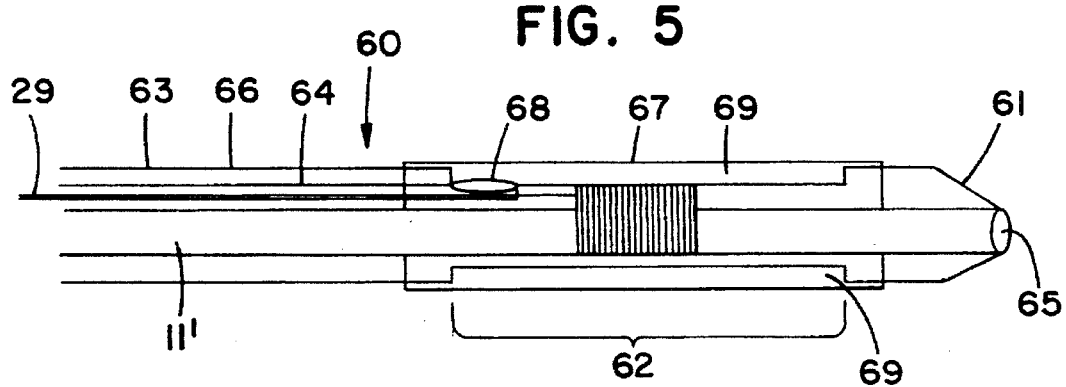
FIG. 5 is a fragmentary view, partially in section, of a still further alternate design of a drug delivery apparatus in accordance with the present invention in the form of a catheter with a drug delivery component to transport a drug to an internal body tissue.
Figure 6:
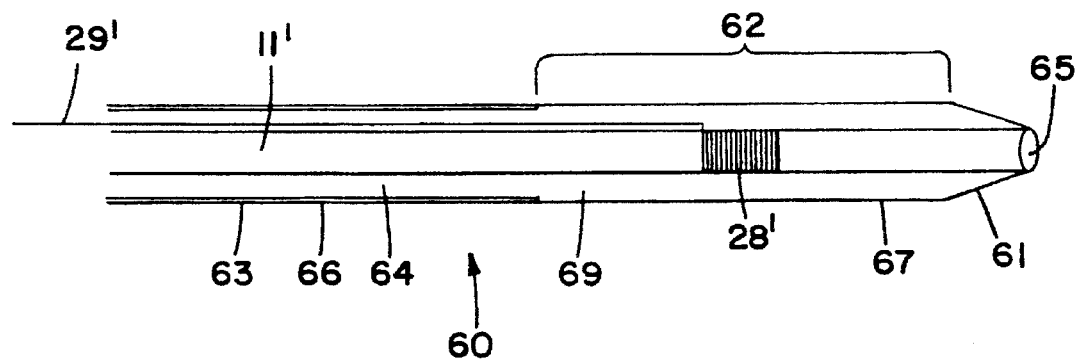
FIG. 6 is a fragmentary view, partially in section, of a still further alternate design of the drug delivery apparatus for drug transport to an internal body tissue in which a selectively permeable membrane forms a portion of the outer wall of the drug delivery component.
Figure 7A:
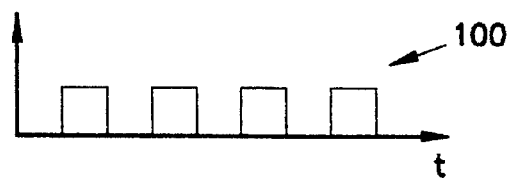
FIGS. 7A–7F depict a variety electric waveforms for use in iontophoresis with the catheters of the present invention.
Figure 7B:
Figure 7C:
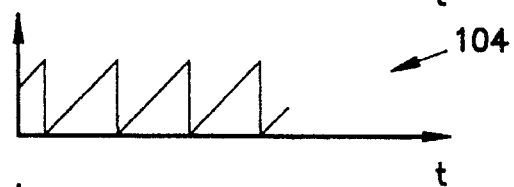
Figure 7D:
Figure 7E:
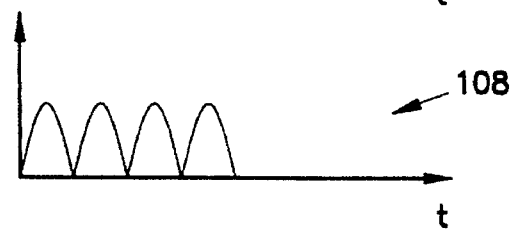
Figure 7F:
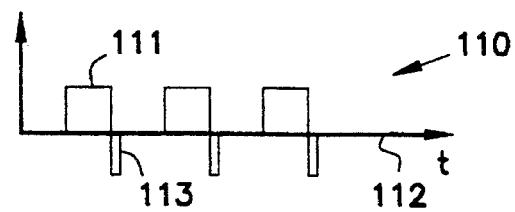

FIGS. 5 and 6 illustrate further alternate designs of the drug delivery apparatus in accordance with the present invention. The embodiments shown in these figures are specifically designed to provide means and a system for delivering a drug or combination of drugs to a localized area of an internal body tissue. For this purpose the apparatus includes a flexible catheter connected to a drug delivery component having a fluid delivery passageway with an outer wall and selectively permeable outer membrane portion through which a drug passes to an internal body tissue target area.

In particular, catheters are commonly used in percutaneous transluminal coronary angioplasty (PTCA) procedures to dilate stenosed blood vessels or arteries. These include so-called over the wire catheters of the type illustrated generally in U.S. Pat. No. 4,323,071, the disclosure of which is incorporated herein by reference, and so-called fixed wire catheters of the type illustrated in U.S. Pat. No. 4,582,181, the disclosure of which is incorporated herein by reference. These catheters may be modified according to the present invention.

Figure 1:
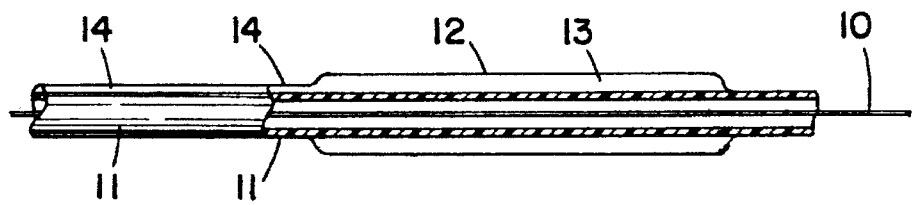
FIG. 1 is a fragmentary view, partially in section, of a first embodiment of the drug delivery apparatus of the type employing the present invention in the form of a catheter with a modified dilatation balloon in its deflated state.

FIG. 1 illustrates the distal end of a catheter with the modified catheter balloon in its deflated state. The catheter includes a guide wire 10, an elongated, flexible catheter body 11, a drug delivery means in the form of a balloon 12 positioned on the catheter body 11 near its distal end and a balloon lumen or passageway 14 extending along the catheter body 11 to the proximal end of the body 11 for inflation and deflation of the balloon 12. In the preferred embodiment, the material from which the balloon 12 is constructed is a permeable or semipermeable material which is effective to permit transport or passage of the fixative or other drug across the balloon surface as a result of iontophoresis according to the present invention.

The structure of the guide wire 10, the catheter body 11 and the balloon lumen 14 is similar to conventional catheter design which is known in the art and an example of which is shown in U.S. Pat. No. 4,323,071. The balloon 12 of FIG. 1, however, is distinguishable from conventional catheter balloons in that the balloon 12 is constructed from a material which selectively permits the transport or passage of a drug or fixative across the balloon surface.

Figure 2:
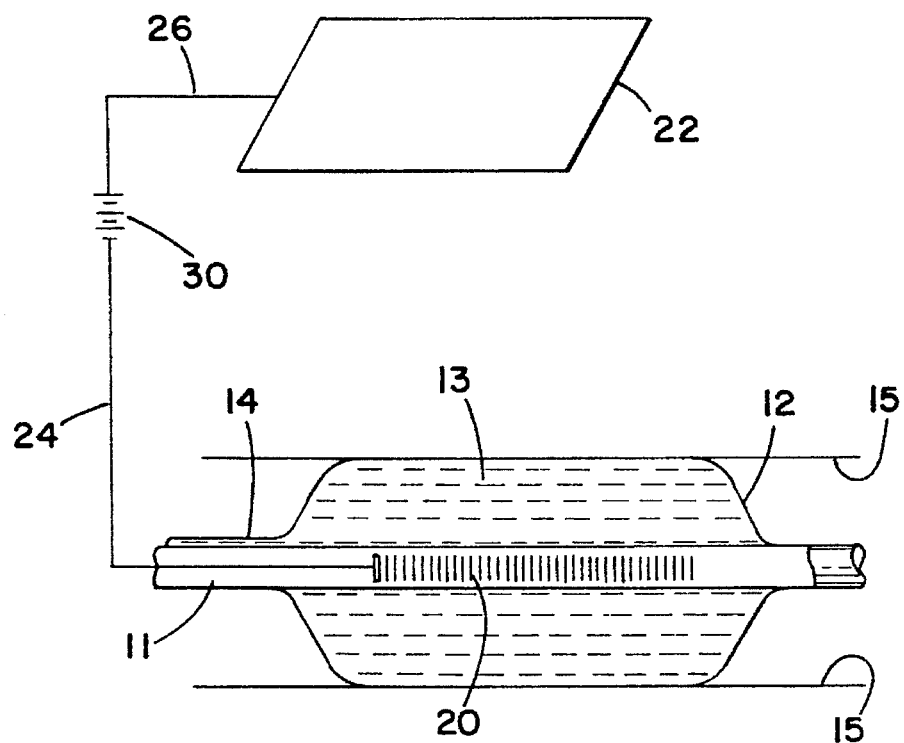
FIG. 2 is a fragmentary view, partially in section, of the drug delivery apparatus of the present invention positioned in a blood vessel depicting iontophoresis means to transport the drug across the balloon surface.

FIG. 2 illustrates the drug delivery apparatus of FIG. 1 with a preferred embodiment of the iontophoresis means depicted. The balloon 12 is in its inflated state within an arterial vessel in which the vessel walls are indicated by the reference numeral 15. During intravessel procedures, such as PTCA, the guide wire 10 is first inserted into the selected artery to a point past the stenotic lesion. The dilatation catheter including the catheter body 11 and balloon 12 is then advanced along the guide wire 10 to the desired position in the arterial system in which the balloon portion 12 traverses or crosses the stenotic lesion. The balloon 12 is then inflated by introducing an inflation fluid through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion. In accordance with the present invention, and in particular in accordance with the embodiment of FIGS. 1 and 2, the balloon 12 is inflated by introducing a fixation or other drug solution through the balloon lumen 14 and into the interior of the balloon portion 12.

Iontophoresis technology is known in the art and is commonly used in transdermal drug delivery. In general, iontophoresis technology uses an electrical potential or current across a semipermeable barrier to drive ionic fixatives or drugs or drag nonionic fixatives or drugs in an ionic solution. Iontophoresis can be useful in certain applications of the present invention because it facilitates both transport of the fixative or drug across the selectively permeable membrane and enhances tissue penetration. In the application of iontophoresis, two electrodes, one on each side of the barrier, are utilized to develop the required potential or current flow. In particular, one electrode may be located inside of the catheter in opposed relation to the drug delivery wall of the catheter while the other electrode may be located at a remote site on a patient's skin.

The embodiment of FIG. 2 illustrates a structure utilizing iontophoresis to assist in driving the fixative or other drug across the balloon wall 12 and into contact with the vessel walls 15. In FIG. 2, one electrode 20, the catheter electrode, is located on or within the catheter body 11 while the other electrode 22, the body surface electrode, is located on the body surface or within the body of the patient. In order for iontophoresis techniques to be utilized, the fixative or other drug within the balloon chamber 13 requires specific characteristics. Ideally, such fixative or other drug should have an ionic nature or have other ionic molecules bound to the fixative or the active components of the drug to promote the iontophoretic movement or transport across the balloon wall 12. An electrical current for the iontophoretic process of FIG. 2 is produced between the electrodes 20 and 22 by an external power source 30 through the electrical leads 24 and 26, respectively.

During operation of the device of FIG. 2, the balloon 26 is first positioned across the stenotic lesion in the manner described above. The balloon interior 13 is then inflated with the fixative through the lumen 14. This is followed by activating the power supply 30, thereby creating a net flow of current between electrode 20 and electrode 22 which passes through the balloon wall 12. In the preferred method, the net current flow drives or drags the fixative or other drug within the chamber 13 across the wall and into contact with the surrounding vessel wall 15 and vascular tissue. The structure of FIG. 2 utilizes both pressure and iontophoresis as the driving force, although, it is contemplated that iontophoresis could be utilized alone.

It is also contemplated that iontophoresis by itself, or in combination with a solvent like DMSO as a carrier, could yield fixative or drug transport into or through a vessel wall at pressures less than about 20 mm Hg above normal ambient vessel wall pressure and preferably at less than about 5 mm Hg, thereby avoiding substantial damage to the vessel wall known to occur at higher pressures.

Additionally, the polarity of the iontophoretic electrodes may be reversed to create a net flow of current in the opposite direction to recapture excess fixative or drug delivered to or through the vessel wall.

Alternatively, the catheter of FIGS. 1 and 2 may be used after dilation has already been effected by another catheter earlier used to dilate the vessel. In this case, the fixative delivering catheter is expandable in order to bring the balloon 12 in contact with the vessel wall for drug delivery.

In the preferred embodiment, it is contemplated that the material from which the balloon of FIGS. 1 and 2 is constructed will be a semipermeable membrane material such as dialysis membrane (Cordis Dow 3500-cellulose acetate and Cordis Dow cellulose regenerated from acetate; anisotropic polyacrylonitrile available from Ashaki Medical). It is contemplated, however, that various other permeable, microporous or semipermeable materials may also be used including, without limitation, cellulose, cellulose acetate, polyvinyl chloride, polysulfone, polyacrylonitrile, silicon, polyurethanes, natural and synthetic elastomers. Examples of suitable microporous membranes are polyester, polyolefin, a fluoropolymer, or the like having pore sizes smaller than 1 micron and preferably from about 10 Å to 1 micron, with a nominal pore size of about 150 Å.

It is contemplated that the particular material from which the balloon 12 is constructed will depend to some extent on the specific composition of the fixative or other drug to be delivered as well as the driving pressures which may be developed within the balloon chamber 13. In the structure of FIGS. 1 and 2, the preferred material from which the balloon 12 is constructed is an elastomer and the pressure generated within the balloon chamber 13 to aid in transport of the drug or fixation solution across the balloon walls is between about 1 and about 90 psi.

Figure 3:
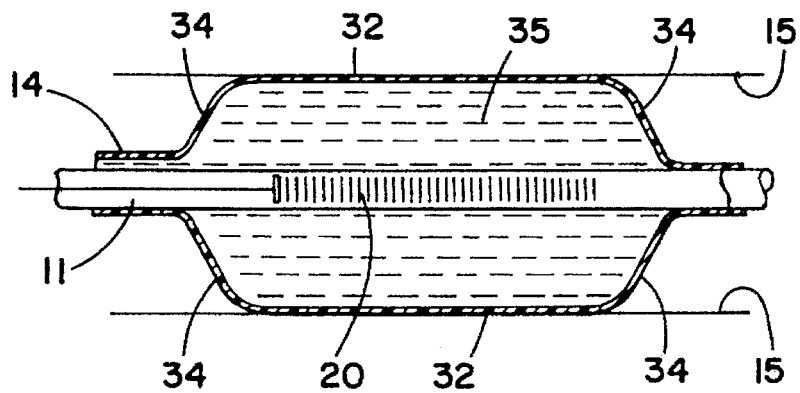
FIG. 3 is a fragmentary view, partially in section, of a further embodiment of the drug delivery apparatus of the present invention positioned in a blood vessel.

A further modified balloon structure is illustrated in FIG. 3. The embodiment of FIG. 3 is similar to the embodiment of FIGS. 1 and 2 except that the balloon structure in FIG. 3 is constructed of two different materials. It will be appreciated that as an alternative, the balloon structure in FIG. 3 can be constructed of a permeable material that is modified to have one or more impermeable portions (i.e., increased thickness). In FIG. 3, the balloon end portions 34 are a totally impermeable material, while an intermediate portion 32 of the balloon positioned between the end portions 34 is a permeable or semipermeable material. The purpose of this structure is to enable more specific and precise delivery of the fixation solution or other drug desired to be administered. For example, with the end portions 34 constructed of an impermeable material, inadvertent passage of the fixation solution or other drug through such end portions is prevented. In the structure of FIG. 3, the impermeable material may be polyethylene, or polyester or an area of permeable material that is functionally impermeable because of increased thickness or other modification that results in a non-permeable region or regions.

In the structure of FIG. 3, the fixative or other drug is permitted to pass from the interior chamber 35 of the balloon only through the balloon portion 32. The material from which the portion 32 is constructed is similar to the material from which the balloon 12 of FIGS. 1 and 2.

As a further alternative, the catheters of FIGS. 1–3 may be coated on their outer surfaces, or at least that portion of the outer surface which is to contact the vessel wall, with hydrogel to improve contact with the vessel wall. The hydrogel so described may also contain the fixative or drug to be delivered where solution passing from the catheter through the hydrogel will dissolve the fixative or drug and transport the fixative or drug to the vessel wall. As a further alternative, drug impregnated hydrogel may be coated on the inside wall of a catheter for similar drug delivery as solution passes through the hydrogel and catheter wall.

In the embodiments of FIGS. 1–3, iontophoresis and pressure are the force which can be utilized to transport the fixative or other drug from the interior balloon chamber across the balloon wall to the vessel wall. However, it is contemplated that other transport forces could also be used either with or in lieu of pressure to enhance or otherwise control the speed of drug transport using the preferred mode of iontophoresis. For example, one method could utilize DMSO as a carrier to transport a fixative or drug through the vessel wall. Other fluid diffusion enhancement compositions include propylene glycol, azone and ionic or non-ionic surfactants.

Figure 4:
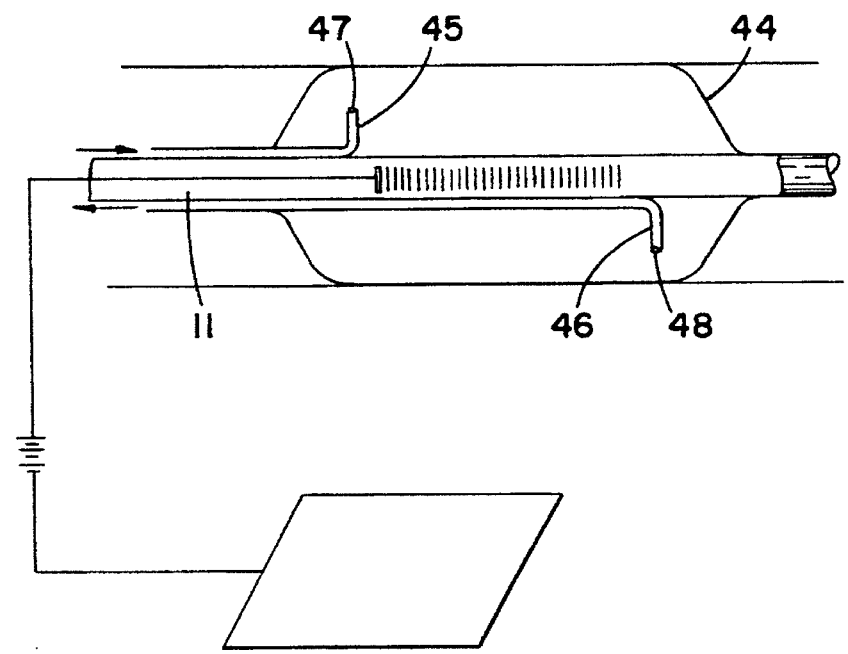
FIG. 4 is a fragmentary view, partially in section, of the drug delivery apparatus of the present invention positioned in a blood vessel, embodying iontophoresis to transport a drug across the balloon surface where the solution containing the drug is circulated through the balloon.

A still further embodiment of a drug delivery apparatus in accordance with the present invention is illustrated in FIG. 4. This embodiment would be useful for delivery of a fixative, but would be particularly useful for delivery of antitumor drugs. FIG. 4 illustrates a modified catheter balloon design having a balloon 44 positioned on catheter body 11 near its distal end. One delivery lumen or passageway 45 extends along the catheter body 11 to the proximal end of the body 11 and a recovery lumen or passageway 46 also extends along the catheter body 11 to the proximal end, said delivery lumen 45 and recovery lumen 46 useful for circulating solution containing a fixative or drug to and from the catheter balloon. The outlets 47 and 48 may be positioned in the balloon to achieve optimal circulation within the balloon. This embodiment may be most useful in delivering antitumor drugs which are difficult to dissolve where the delivery solution accordingly is very low in concentration of the antitumor drug and easily depleted of such drug. Circulation in this case would be important for continuous delivery over long time periods. This embodiment may be combined with reversing the polarity of the electrodes of iontophoresis in order to remove excess drug after treatment.

In addition to the embodiment of FIG. 4, the embodiments of FIGS. 1–3, illustrated principally for delivery of a fixative to a vessel wall, can also be useful in delivering any drug to or through a vessel wall. In particular, each of the above embodiments of FIGS. 1–4 may be used for such drug delivery and each embodiment would be useful for delivering an antitumor, antihyperplastic or other agent through a vessel wall to a nearby or adjacent tumor or other internal body tissue. For example, a drug may be delivered substantially transversely to the longitudinal axis of a body passageway in order to treat a localized region of tissue located adjacent to the passageway. This is illustrated by using iontophoresis to drive a drug through the passageway wall and into the surrounding or adjacent tissue either alone or in combination with pressure and/or DMSO. Any of the foregoing alternative embodiments of the apparatus as seen in FIGS. 1–4 may also be used for such drug delivery.

In particular, tumors may be treated by delivering certain drugs through blood vessels or the intestinal tract or whatever to adjacent tumor sites. Further, the present invention is well suited to delivery of sensitizer and immunomodulator drugs.

For the purposes of primary or adjuvant treatment or other circumstances where drug delivery to a specific local or regional internal body tissue site such as a solid tumor, abscess, regional lymph nodes or the like is desired, further embodiments of the present invention as shown in FIGS. 5 and 6 are preferred. The tissue delivery system shown in FIGS. 5 and 6 includes a drug delivery apparatus 60 that is positioned into a specific tissue, such as a tumor.

As seen in FIG. 5, a preferred drug delivery apparatus 60 for treating an internal body tissue includes a flexible catheter body 11' and drug delivery component 69 having a drug delivery passageway 64 including an outer wall 66, and an outer selectively permeable membrane portion 67 proximate the distal end 61. The outer selectively permeable membrane 67 prevents escape of the drug from passageway 64 and drug delivery component 69 until the desired time of delivery. It is to be understood that the selectively permeable membrane 67 also controls the rate of release of the drug. The drug is then driven across membrane 67 by a voltage gradient (iontophoresis) or other force. In a preferred embodiment for iontophoresis, selectively permeable membrane 67 material is a dialysis membrane, nylon, or polysulfone. Drug delivery passageway 64 of drug delivery component 69 extends from proximal end 63 to distal end 61 of apparatus 60. As seen in FIGS. 5 and 6, drug delivery component 69 is preferably coaxially aligned about catheter body 11'. It is to be appreciated that drug delivery component 69 can be connected with catheter body 11' by a variety of adjacent configurations by one of skill in the art.

The embodiment seen in FIG. 5 illustrates selectively permeable membrane 67 affixed to a portion of outer wall 66 having at least one opening 68 that facilitate fluid transfer through outer wall 66 of passageway 64 to membrane 67. Alternatively, as seen in FIG. 6, selectively permeable membrane 67 can form an integral portion of outer wall 66. As seen in both FIGS. 5 and 6, to position apparatus 60 over the shaft of an introducer such as a probe, needle or trocar (not shown) introducer lumen 65 through the center of catheter body 11' is provided. It is to be understood that apparatus 60 can range in size from very large (trocar) to very small (tenths of mm), depending on the type and location of internal body tissue to be treated.

The embodiments of apparatus 60 in FIGS. 5 and 6 utilize iontophoresfs to assist in driving the drug across selectively permeable membrane 67. To deliver a drug to a target area of an internal body tissue, iontophoresis is preferred because it facilitates both transport of a fixative or drug across the selectively permeable membrane and enhances tissue penetration. If iontophoresis is used, then similarly to the structure seen in FIG. 2, one electrode 28', the catheter electrode, is located on or within catheter body 11', while the other electrode (31) is located on the body surface of the patient. The other electrode may in certain applications be positioned at other regions of the patient including appropriate internal areas.

As an alternative to the embodiments seen in FIGS. 5 and 6 using iontophoresis alone to deliver a drug to a target area, the tissue delivery system of the present invention can use pressure as an additional force to transport a drug to a target area of internal body tissue. For this purpose, regulation means known to those skilled in the art (e.g., compressor, regulator or syringe pump) can be used to apply sufficient pressure to deliver the drug to the target area. Those of skill in the art will recognize that the pressure applied in conjunction with iontophoresis will be adequate to drive the drug across selectively permeable membrane 67 to the target area without further traumatization of the internal body tissue to be treated.

As described earlier with respect to the embodiments shown in FIGS. 1–6, other transport forces can be used with iontophoresis to enhance or otherwise control the speed of drug transport to an internal body tissue according to the present invention. For example, one of skill in the art could utilize pressure, DMSO, propylene glycol, azone, or various surfactants as a carrier to transport the drug through selectively permeable membrane portion 67 to the target area of internal body tissue.

For treatment of an internal body tissue according to the present invention, the introducer (not shown) is placed into the target area, which may be a tumor or the like, after identification of the position of the lesion mechanically, radiographically, thermally, ultrasonically, or through some other like methodology. The trocar/probe can be designed for steerability to facilitate positioning into the tumor. This can be accomplished by simply placing a bend in the trocar or by other mechanical design techniques known to those skilled in the art.

The active apparatus 60 is then passed through or over the introducing element directly over the inducer or through the void left in the intervening tissue by the withdrawal of the introducer. After apparatus 60 is in place, as confirmed by one of the foregoing methods, the active compound is delivered through passageway 64 into drug compartment 69 and across membrane 67 into the local or regional tissue. Using an embodiment of apparatus 60 of the type seen in of FIGS. 5 or 6, the delivery is accomplished iontophoretically. The active compounds delivered to an internal body tissue using apparatus 60 include, but are not limited to, antitumor agents such as the vinca alkaloids, anthracycline antibiotics, platinum analogs, antimetabolites (e.g., methotrexate); antibiotics; sensitizers or other compounds.

The advantage of this method is that it allows delivery of the drug into the interstitial fluid and into the cells of the target area themselves even if the vasculature of the area is severely compromised and the cells do not preferentially take up the drug. These phenomena are a well-known attribute of solid tumors and constitute one of the most significant barriers to the treatment of such cancers.

In addition to delivery of antitumor agents to internal tissues, the usefulness of the present apparatus and method for the treatment of other diseases of internal tissue will be appreciated by those skilled in the art.

According to the present invention, further catheter embodiments are envisioned employing a selectively permeable microporous membrane portion of the drug delivery component, together with the iontophoresis means of the present invention to transport drugs to a body tissue. In these embodiments, the microporous membrane, in conjunction with the active delivery mechanisms, aids in controlling drug transfer from the catheter by minimizing passive diffusion or flow under the slight pressure involved in filling the drug chamber or inflating the balloon to make contact with a vessel wall. However, drug delivery into the tissue under active iontophoretic delivery will not be inhibited by the membrane.

The microporous material provides more uniform delivery areas, which will provide more uniform drug distribution into the surrounding tissue, will reduce the potential for areas of high current densities during iontophoresis (associated with a few larger pores), and will decrease the potential for tissue damage or breakdown of the membrane material due to high current density.

The numerous micropores also reduce the likelihood that a significant portion of the membrane could become blocked with blood components, secretions, lubricants, or other material. In addition, blood or other secretions will not cross the microporous membrane and enter the drug chamber during deflation of the balloon. The microporous material will also allow rapid balloon deflation without blood reflux into the catheter, which is an important feature in coronary arterial applications. Finally, the microporous material will allow the use of a neutral or charged membrane surface to promote or control drug transfer and delivery.

The microporous membrane can have either an isotropic (asymmetric) or symmetric structure. The pore size of the membrane can vary from about 10 Å to 10,000 Å (i.e., 1 micron). Microporous membranes that satisfy the requirements of the invention can be manufactured in any of several ways, most of which are readily understood by those skilled in the art of manufacturing microfiltration and ultrafiltration membranes.

Further descriptions of catheters employing microporous membranes useful with the present invention are described in U.S. patent application titled DRUG DELIVERY APPARATUS AND METHOD, filed on Aug. 28, 1992 by James E. Shapland, Mark B. Knudson, and Jin Shimada; which is incorporated by reference above.

The various embodiments of preferred catheters described above are all adapted to use iontophoresis as a driving force to transport a drug and/or fixative across a membrane. Direct current is theorized to be most effective for iontophoresis, although, as discussed above, direct current may cause cardiac arrhythmias, vascular spasms, muscle stimulation and other undesirable side effects.

The present invention involves the use of electrical waveforms which provide a net flow of current to or from the catheter electrodes. Possible waveforms contemplated for use in the invention are depicted in FIGS. 7A–7F and include square waves 100, rectangular waves 102, saw-toothed waves 104, sinusoidal waves that do not reverse polarity 106, rectified sinusoidal waves 108, and modified rectangular waves 110 (or other waveform shapes as desired) which do reverse polarity but provide a net flow of current in a desired direction.

The primary characteristic of the preferred waveforms used in the present invention is that they all provide net flow of current from the catheter electrode. The majority of the preferred waveforms never reverse polarity, while others can reverse polarity briefly to provide better control over the inducement of cardiac arrhythmias. Even in those waveforms which do reverse polarity, however, there is a net flow of current in one direction as depicted by waveform 110 in FIG. 7F. Current flow in a first direction is indicated by area 111 above line 112 and current flow in a second (opposite) direction is indicated by area 113 below line 112. As a result, summing the areas 111 and 113 shows a net positive flow of current in the first direction as area 111 is larger than area 113.

The frequency of any waveforms used in the present invention can be varied to provide the maximum iontophoretic transfer rate while avoiding potential problems caused by the electrical current. The preferred frequency range begins at about 200 Hz and increases to a maximum of about 100 kHz, with the most preferred range lying between 5–15 kHz. It will be understood that the frequency can be varied within these ranges to maximize the rate of iontophoretic transfer for a given drug or fixative used in the catheters of the present invention.

Figure 8A:
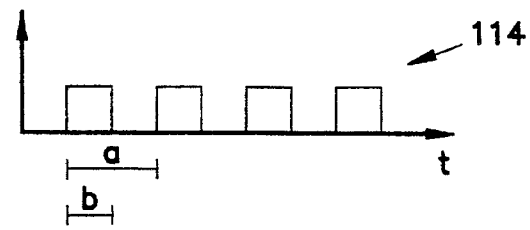
FIGS. 8A & 8B depict two rectangular electric waveforms for use in iontophoresis with the catheters of the present invention.
Figure 8B:
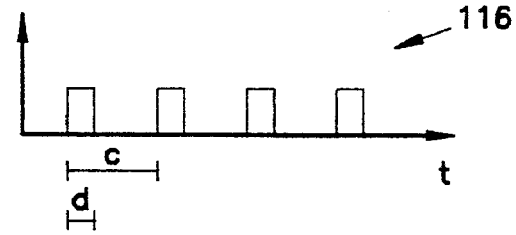

One preferred embodiment waveform is a rectangular waveform. Such a waveform has a duty cycle that is determined by the ratio of the time that the current is flowing to the time that no current is flowing. As depicted in FIGS. 8A & 8B, the duty cycle of the rectangular waveform 114 is b/a while the duty cycle of waveform 116 is d/c. The preferred range for the duty cycle is broad, i.e., between 5–95%, with a nominal value of 50%.

Figure 9:
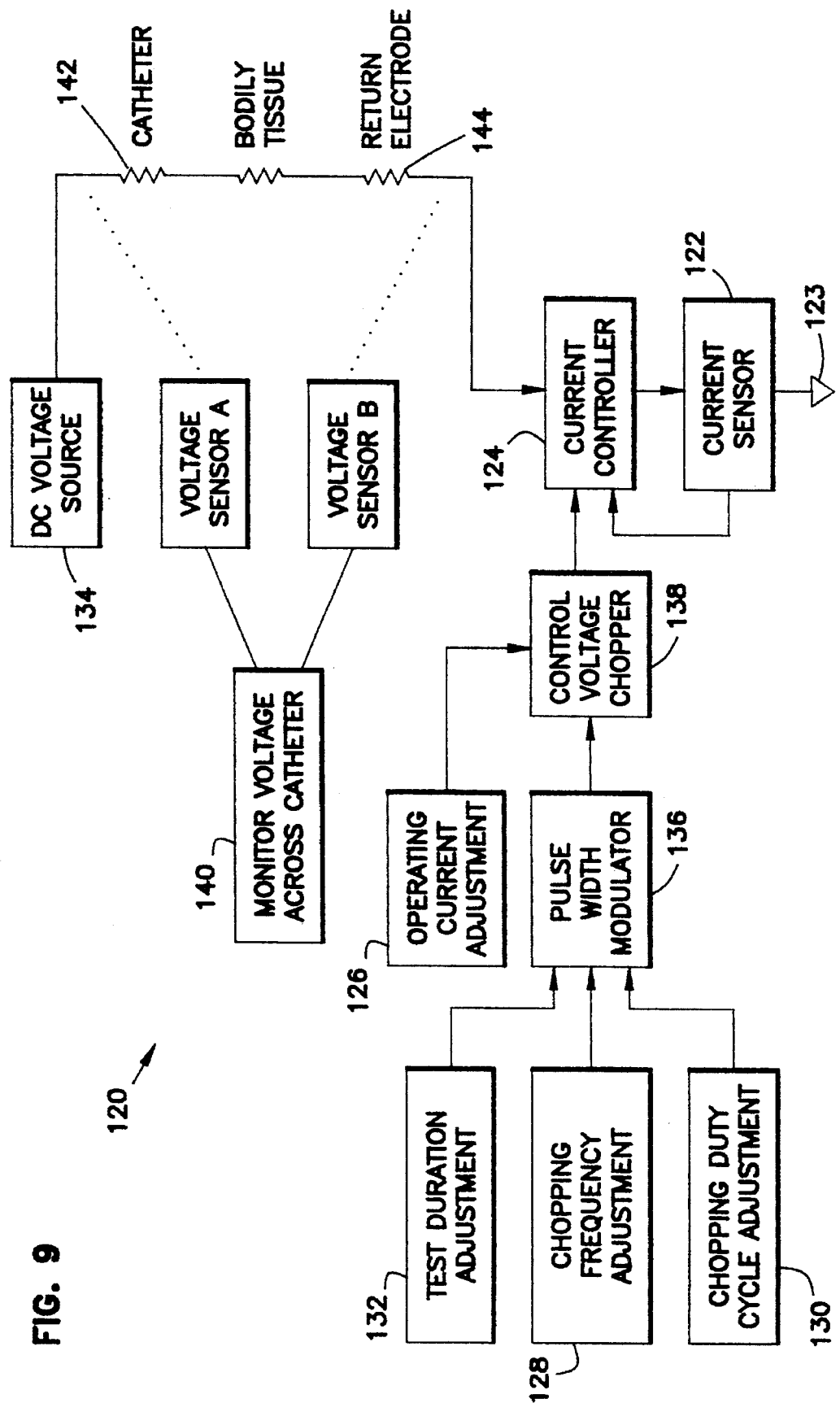
FIG. 9 depicts a block diagram of the preferred circuit used to supply the electric waveforms for use in iontophoresis with the catheters of the present invention.

FIG. 9 depicts a block diagram of the preferred electrical circuit 120 used to provide the waveforms described above. The circuit 120 must provide waveforms with the required frequency and duty cycle and must also deliver the desired current under varying impedances encountered by the catheter in surrounding tissues and fluids.

The preferred circuit 120 incorporates a current sensor 122 and a current controller 124 used to monitor the actual current levels delivered at the catheter and adjust the voltage to maintain a desired current level. The current sensor 122 is preferably connected to an isolated ground 123 to ensure the accuracy of the current sensor readings. The reaction time of this portion of the circuit 120 is preferably about 100 microseconds to prevent unwanted changes in the current due to sudden changes in the impedance of the catheter system (including surrounding body tissues).

The preferred circuit also includes adjustments for setting a desired current level 126, waveform frequency 128 and duty cycle 130. Because the preferred waveform is rectangular, the frequency and duty cycle are both preferably controlled by adjusting a chopper to provide the desired values. The preferred circuit also includes a test duration adjustment 132. Each of the above adjustments are optional and, in their place, a set configuration can be designed in the circuit 120.

Voltage across the circuit is supplied by a DC voltage supply 134 and a pulse width modulator 136 and control voltage chopper 138 are used to produce the actual desired waveform.

The voltage sensor 140 depicted in FIG. 9 is optional, but does supply a means to measure and display the voltage used to produce the desired current.

FIG. 9 also depicts the catheter electrode 142 and return electrode 144. The catheter electrode is incorporated into the drug delivery chambers of the preferred catheters. Examples include electrode 20 in FIGS. 2 & 3 and 28' in FIG. 6.

The surface area of the electrodes used in the present invention should be as large as possible to allow desired current levels to be maintained while preventing undesired oxidative/reductive reactions from occurring at the electrode. The surface area can be increased by using coils, as depicted in FIG. 5, or other geometric shapes which increase the surface area of the electrode. In addition, the surface of the electrode can be roughened to increase the exposed surface area.

The preferred electrode materials should minimize undesired oxidative/reductive reactions or production of competitive ions during the iontophoresis. The preferred electrode materials are silver for anodal electrodes and silver/silver chloride for cathodal electrodes.

The return electrode, depicted as reference number 144 in circuit 120 and as reference number 22 in FIG. 2, is preferably positioned on the surface of the patient's body. Research has shown that the position of the return electrode has little to no effect on the rate or directionality of the transfer. The preferred electrode has pressure-sensitive adhesive backing and a low impedances at the skin to electrode interface. The surface area of the electrode is preferably 1–100 $cm^2$ to insure current density of less than 0.5 mA/$cm^2$ in the preferred embodiments and methods.

Although the description of the preferred embodiments and methods have been quite specific, it is contemplated that various modifications could be made without deviating from the spirit of the present invention. For example, a fixative or other drugs may be delivered to the walls of an artery, perhaps already dilated, through a catheter balloon wall which is perforated. An antitumor drug may be similarly delivered through a perforated balloon wall for delivery through a vessel wall to an adjacent tumor. Such perforated balloons are combined with iontophoresis to drive the drug into or through the vessel wall. Further, a drug can be delivered to an internal body tissue through a selectively permeable membrane portion of a drug delivery component connected to a catheter. When the catheter and connected drug delivery component are directed to a body tissue target area over a rigid probe or trocar the amount of drug delivered to the tissue to be treated is maximized and the leakage of drug back along the catheter and away from the target area is minimized. Also, many different waveforms other than those specifically mentioned could be used. Accordingly, it is intended that the scope of the present invention be dictated by the appended claims, rather than by the description of the preferred embodiment and method.

We claim:

1. A method of delivering a drug to a target area of internal body tissue adjacent to a patient's heart, the method comprising the steps of:
   (a) inserting a catheter into said target area of a body, said catheter comprising a distal end for local delivery of said drug, a fluid delivery passageway, an outer wall, a permeable outer membrane portion proximate said distal end, and iontophoresis means proximate said permeable membrane for iontophoretic transport of said drug across said permeable outer membrane without application of pressure;
   (b) supplying net flow of electric current in a desired direction to said iontophoresis means to deliver said drug to said target area; and
   (c) varying said electric current with time to provide a waveform having a frequency of about 200 Hz or higher such that the rate of iontophoretic transport of said drug is increased and the risk of inducing cardiac arrhythmias during iontophoretic transport is decreased.

2. The method of claim 1, wherein said electric current is supplied with a waveform chosen from the following group: square wave, rectangular wave, saw-toothed wave, sinusoidal wave which does not reverse polarity, rectified sinusoidal wave, or modified wave which reverses polarity but provides said net flow of electric current in said desired direction.

3. The method of claim 2, wherein said waveform has a frequency of between about 5 kHz to about 15 kHz.

4. A method of delivering a drug to a local area of an internal body passageway adjacent to a patient's heart having an elongated passageway wall, the method comprising the steps of:
   (a) inserting a catheter having a distal end and a proximal end into said internal body passageway, said catheter further comprising a balloon near the distal end of the flexible catheter for engagement with a wall of said local area of said passageway, said balloon having an outer wall with a permeable drug transport portion and a drug delivery chamber, a drug delivery lumen extending from said drug delivery chamber to said proximal end of said flexible catheter, and iontophoresis means proximate said distal end for iontophoretic transport of said drug across said permeable outer membrane without application of pressure;
   (b) supplying a net flow of electric current in a desired direction to said iontophoresis means to deliver said drug to said area local of said internal body passageway; and
   (c) varying said electric current with time to provide a waveform having a frequency of about 200 Hz or higher such that the rate of iontophoretic transport of said drug is increased and the risk of inducing cardiac arrhythmias during iontophoretic transport is decreased.

5. The method of claim 4, wherein said electric current is supplied with a waveform chosen from the following group: square wave, rectangular wave, saw-toothed wave, sinusoidal wave which does not reverse polarity, rectified sinusoidal wave, or modified wave which reverses polarity but provides said net flow of electric current in said desired direction.

6. The method of claim 5, wherein said waveform has a frequency of between about 5 kHz to about 15 kHz.

7. A method of iontophoretically delivering a drug to a target area of internal body tissue adjacent to a patient's heart, the method comprising the steps of:
   (a) inserting a first electrode into a lumen proximate the internal target area of a body;
   (b) placing a second electrode in contact with the patient's body;
   (c) delivering said drug into the lumen proximate the target area and the first electrode;
   (d) supplying a net flow of electric current between said first and second electrodes, said electric current iontophoretically delivering the drug to said target area; and
   (e) varying said electric current with time to provide a waveform having a frequency of about 200 Hz or higher.

8. The method of claim 7 wherein said electric current waveform is supplied with a waveform chosen from the following group: square wave, rectangular wave, saw-toothed wave, sinusoidal wave which does not reverse polarity, rectified sinusoidal wave, or modified wave which reverses polarity but provides said net flow of electric current in said desired direction.

9. The method of claim 8 wherein said frequency does not exceed about 100 kHz.

10. The method of claim 8 wherein said waveform has a frequency of between about 5 kHz to about 15 kHz.

* * * * *

UNITED STATES PATENT AND TRADEMARK OFFICE
CERTIFICATE OF CORRECTION

PATENT NO. :   5,499,971

DATED       :   March 19, 1996

INVENTOR(S) :   Shapland et al.

It is certified that error appears in the above-identified patent and that said Letters Patent is hereby corrected as shown below:

Title page, insert item
[75], Inventors, line 2 "Hildebrandt" should read --Hildebrand--

Col. 9, line 21 "iontophoresfs" should read --iontophoresis--

Col. 14, line 3 "area local" should read --local area--

Signed and Sealed this

Twenty-fourth Day of December, 1996

Attest:

BRUCE LEHMAN

Attesting Officer

Commissioner of Patents and Trademarks